United States Patent [19]

Goor et al.

[11] 4,429,701

[45] Feb. 7, 1984

[54] METHOD AND APPARATUS FOR MEASURING THE SYSTEMIC VASCULAR RESISTANCE OF A CARDIOVASCULAR SYSTEM

[76] Inventors: Daniel Goor, 4 Uri St., Tel Aviv; Raphael Mohr, Shikun Rofim 19/6, Tel Hashomer, both of Israel

[21] Appl. No.: 304,596

[22] Filed: Sep. 22, 1981

[51] Int. Cl.$^3$ ............................................. A61B 5/02
[52] U.S. Cl. .................................................. 128/713
[58] Field of Search ............................. 128/671–675, 128/677, 691–694, 700, 713

[56] References Cited

U.S. PATENT DOCUMENTS 4,203,451   5/1980   Panico ................................. 128/672

OTHER PUBLICATIONS

Brower; R. et al., "A Device for the Calculation of dP/dt/P with Internal Calibration", IEEE Transactions on Biomed Engrg., vol. BME-21, No. 1, Jan. 1974.
George; M. et al., "Measurement of the Maximum Rate of Rise of Aortic Blood Pressure in Man", Med. Research Engrg., 1967, pp. 21–24.

Primary Examiner—Kyle L. Howell
Assistant Examiner—Francis J. Jaworski
Attorney, Agent, or Firm—Benjamin J. Barish

[57] ABSTRACT

In the described method and apparatus for examining a subject's cardiovascular system, a blood-pressure signal having a waveform varying in accordance with the subject's arterial pressure is differentiated to produce a dP/dt signal having a waveform varying in accordance with the rate at which the blood-pressure signal varies. The pressure at the time of the peak dP/dt signal is detected and is divided by the dP/dt signal to produce a measurement corresponding to the systemic vascular resistance. The latter measurement is then multiplied by a resistance factor corresponding to the physical resistance characteristic of the particular cardiovascular system examined. A measurement of the cardiac output may also be produced by subtracting, from the mean arterial pressure of the subject, the subject's central venous pressure and dividing the latter by the systemic vascular resistance.

19 Claims, 2 Drawing Figures

METHOD AND APPARATUS FOR MEASURING THE SYSTEMIC VASCULAR RESISTANCE OF A CARDIOVASCULAR SYSTEM

BACKGROUND OF THE INVENTION

The present invention relates to a method and apparatus for examining and indicating the status of the cardiovascular system of a subject. The method and apparatus are both particularly useful for measuring the systemic vascular resistance, and also for measuring the cardiac output of the subject, by detecting the subject's arterial pressure and processing same in a particular manner as described below.

A number of measurements relating to a subject's cardiovascular system are useful in assessing its status, these measurements including the mean arterial pressure (MAP), central venous pressure (CVP), cardiac output (CO), and the systemic vascular resistance (SVR), sometimes called the total peripheral resistance (TPR). These measurements have the following relationships: $MAP - CVP \approx CO \times SVR$; this relationship will be recognized as the cardiovascular equivalent of Ohm's law of electricity ($E = I \times R$). The mean arterial pressure (MAP) can be obtained by electrical damping or by calculation of the following relationship:

$$MAP = DP + \frac{1}{3}(SP - DP)$$

wherein DP=diastolic pressure, and SP=systolic pressure. The arterial "pulse pressure" is the difference between the systolic and diastolic pressure, and is dependent on the stroke volume, arterial capacitance, and run-off.

The arterial pressure is commonly measured directly by one of several known techniques, including both non-invasive techniques such as by the use of the Riva-Rocci occlusive cuff, and invasive techniques such as by the use of catheters placed in various arteries, particularly a radial artery or a femoral artery. Cardiac output (CO) is usually measured by a thermal dilution or dye dilution technique; and the systemic vascular resistance (SVR) is usually derived from these measurements according to the above relationship.

A serious drawback in the above techniques for assessing the status of a subject's cardiovascular system is the invasive nature of the procedures used today for measuring cardiac output. The cardiac output, being the amount of blood pumped to the peripheral circulation by the heart per minute, reflects the status of the entire circulatory system, not just the heart, and is an important measurement in assessing the status of the patient's cardiovascular system. The most common technique used today is the thermal dilution procedure employing the Swan-Ganz catheter, in which a cold or iced indicator (e.g. a 5% dextrose solution in water at a temperature of 4° C.) is injected, usually into the heart's right atrium, and the filling pressures of both the right and left sides of the heart are measured by an introduced catheter. Another indicator dilution method uses a green dye and involves the rapid injection of a precise amount of the dye into the central venous circulation, the indicator passing rapidly through the heart and lungs into the arterial circulation where it is detected by sampling arterial blood and passing it through a densitometer. These known techniques are invasive, involve complicated procedures requiring highly-skilled personnel, and are not suited for continuous monitoring.

The above difficulties in the presently known techniques for measuring cardiac output also apply to the measurement of systemic vascular resistance, since that measurement is usually derived (from the above-described relationship) after the mean arterial pressure and the cardiac output have been calculated or otherwise determined.

SUMMARY OF THE INVENTION

An object of the present invention is to provide a new method and apparatus, having advantages in the above respects, for examining and indicating the status of the cardiovascular system of a subject.

The present invention is founded on the discovery, first arrived at purely by empirical means, that the systemic vascular resistance of a cardiovascular system bears a relatively constant relationship to the subject's arterial pressure at the peak of its rate of change divided by the peak of the rate of change of the subject's arterial pressure, i.e., $$SVR = (f) \frac{\text{Pressure at Peak } dP/dt}{\text{Peak } dP/dt}$$

It has also been found that the actual measurement of the systemic vascular resistance depends not only on this relationship, but also on a resistance factor corresponding to the physical elasticity characteristics of the particular cardiovascular system examined. This resistance factor, which has been found to be in the order of 50,000, remains relatively constant for the same individual, and varies relatively little (approximately plus-or-minus 10%) among different individuals. In many applications, it would not be critical to determine the exact value of this factor for the specific individual examined since the actual measurement of cardiac output is less important in such applications than the indication of any changes in the cardiac output; nevertheless, if desired to indicate the actual cardiac output, the exact value of this resistance factor can be separately determined for the individual, e.g., by conventional procedures as will be described more particularly below.

According to a broad aspect of the present invention, therefore, there is provided a method of examining and indicating the status of the cardiovascular system of a subject, comprising the steps:

A. detecting the arterial pressure of the subject and generating in response thereto a blood-pressure signal having a waveform varying in accordance with the detected arterial pressure;

B. differentiating the blood-pressure signal to produce a dP/dt signal having a waveform varying in accordance with the rate at which the blood-pressure signal varies;

C. detecting the peak of the dP/dt signal to produce a peak dP/dt signal;

D. determining substantially the value of the arterial pressure at the time of said peak dP/dt; and E. dividing said latter value by said peak dP/dt signal, thereby producing a measurement corresponding to the systemic vascular resistance of the cardiovascular system.

Preferably, the value of the arterial pressure at the time of the peak dP/dt in step D is determined by actually detecting the arterial pressure at the time of the peak dP/dt, which pressure is divided by the peak dP/dt signal in step E. However, it has been found that the pressure at peak dP/dt is almost equal to the diastolic pressure. Therefore, in order to simplify the method and the apparatus for implement it, in many cases the diastolic pressure may be detected in step D, and used as the dividend in step E, to produce results which are quite close to the above-described preferred method.

The measurement produced in step E may be continuously displayed to provide an indication of the change of the subject's systemic vascular resistance. However, if it is also desired to determine the actual value of the systemic vascular resistance, and not merely to monitor its change, the measurement produced in the above step E may be multiplied by a resistance factor (F) corresponding to the physical resistance characteristics of the particular cardiovascular system examined, as will be described more particularly below.

Further, if it is desired to produce a measurement corresponding to the cardiac output (CO) of the subject, the method would include the further steps of: producing a mean arterial pressure signal having a value corresponding to the mean arterial pressure of the subject; subtracting, from the latter signal, a signal corresponding to the subject's central venous pressure; and dividing the latter signal by the systemic vascular-resistance signal of step F to produce a measurement corresponding to the cardiac output. This measurement may be also continuously displayed.

The invention also provides apparatus including a combination of means to perform the above functions.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

The invention is herein described with respect to a two-channel apparatus, namely: one channel which detects and processes the radial arterial pressure, and a second, separate channel which detects and processes the femoral arterial pressure. This is preferred since, under extreme conditions of high peripheral resistance, there is a difference in the blood-pressure waveforms between a peripheral artery and a central artery. We have found that best results are obtained, particularly under extreme conditions, if both the radial pressure (a peripheral artery) and the femoral pressure (a central artery) are used for detecting the arterial pressure, and the lower value of the two detected pressures is used for processing. Accordingly, the circuit illustrated in FIG. 1 not only includes the two channels for processing the radial pressure and the femoral pressure, but also includes a minimum-level-detector circuit MLD which selects the channel of the lower value of the above two for further processing to determine the total peripheral resistance and also the cardiac output of the examined cardiovascular system. This lower value can be selected automatically by a circuit comparing the two levels, or manually by an operator monitoring the two levels.

Figure 2:
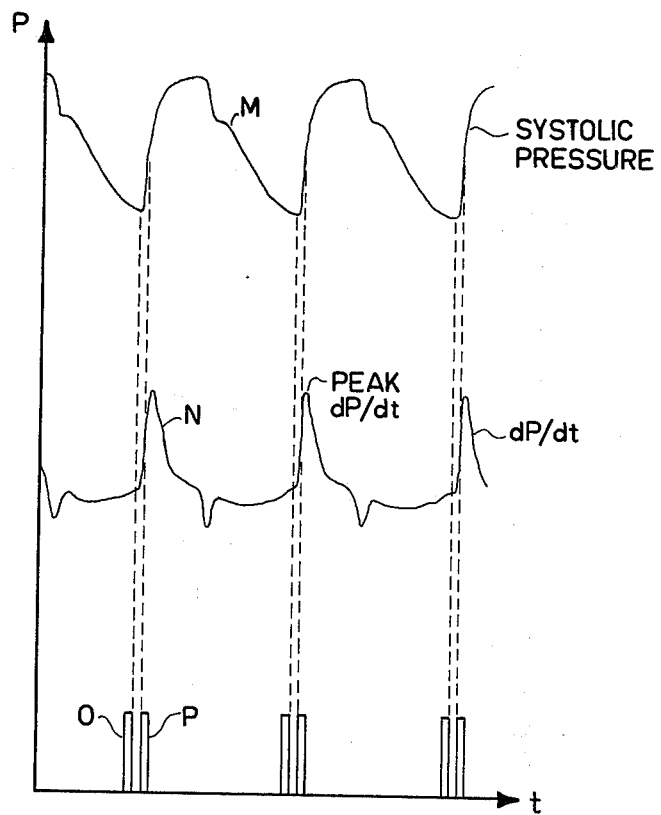
FIG. 2 illustrates typical signal waveforms at various locations of the apparatus of FIG. 1.

The apparatus illustrated in the drawings, and therein generally designated 2, is adapted to be used with a commercially-available instrument for measuring blood-pressure. When both the radial pressure and the femoral pressure are to be detected as indicated above, the apparatus would be used with two of such commercially-available instruments, these being generally designated 10 and 100, respectively, in FIG. 2. Channel 10 is for use in detecting the radial arterial pressure of the patient, and produces a number of electrical outputs, three of which are inputted to the instrument 2 of the present invention, as follows: (a) output 10a is an electrical signal having a waveform (M, FIG. 2) varying in accordance with the detected radial arterial pressure of the subject; (b) output 10b is an electrical signal (a sync pulse) corresponding to the diastolic pressure of the subject; and (c) output 10c is an electrical signal having a value corresponding to the mean arterial pressure of the subject. The second channel 100, used for detecting the femoral arterial pressure of the subject, similarly outputs: (a) at 100a, an electrical signal having a waveform varying in accordance with the detected femoral arterial pressure; (b) at 100b, an electrical signal (a sync pulse) corresponding to the femoral diastolic pressure, and (c) at output 100c, an electrical signal having a value corresponding to the mean femoral arterial pressure.

Since blood-pressure measuring instruments corresponding to channels 10 and 100 are presently commercially available, details of their construction are not set forth herein, and the remainder of the description is directed to the construction and operation of instrument 2 which processes these output signals in a particular manner as described below.

Thus, the radial pressure waveform (M, FIG. 2) outputted at 10a is fed, via a buffer circuit 12, to a differentiator circuit 14, which latter circuit produces a "dP/dt" signal having a waveform (N, FIG. 2) varying in accordance with the rate at which the radial pressure signal at 10a varies. This dP/dt signal is then fed to a peak detector circuit 16 which detects the peak of the dP/dt signal to produce a "peak dP/dt" signal 16s. The peak dP/dt signal 16s is displayed in read-out 18 and is also fed to one input of the above-mentioned minimum-level-detector circuit MLD.

The minimum-level-detector circuit MLD also receives a corresponding peak dP/dt signal 116s from the femoral arterial pressure channel 100 via its corresponding output 100a, which output is processed in a corresponding buffer circuit 112, differentiator circuit 114, and peak detector circuit 116, including peak dP/dt read-out 118.

Circuit MLD also receives, from the radial and femoral arterial pressure channels, a signal corresponding to the arterial pressure at the time of peak dP/dt. Thus, with respect to the radial channel 10, there is provided a sample-and-hold circuit 20 controlled by a bistable device, namely flip-flop 22, which device is actuated to one state (e.g., "set") by the radial diastolic sync (S) pulse 10b, and is actuated to its other (e.g. "reset") by the dP/dt signal from circuit 14, the peaks of which latter signal trigger a monostable multivibrator 24 to control the flip-flop 22. The sample-and-hold circuit 20 receives the arterial pressure signal (M, FIG. 2) and outputs a signal 20s to the MLD circuit which signal (20s) corresponds to the arterial pressure at the time of pulse P in FIG. 1, namely the time when the dP/dt is maximum. This signal 20s is fed into one input of the MLD circuit.

The MLD circuit receives a corresponding signal 120s from the femoral channel (as produced by the sample-and-hold circuit 120 controlled by the flip-flop 122) which in turn is controlled by the femoral diastolic sync (S) pulse 100b and the monostable multivibrator 124 triggered by the differentiator circuit 114.

The minimum-level-detector circuit MLD determines which of the two arterial pressure channels 10 or 100 produces the lower dP/dt signal, and connects that channel to a systemic vascular resistance circuit (SVR) which computes the systemic vascular resistance according to the following relationship:

$$SVR = F \times \frac{\text{Pressure at Peak } dP/dt}{\text{peak } dP/dt}$$

The peak dP/dt pressure signal (16s or 116s) of the thus-selected channel is applied to circuit SVR via its input SVRa, and the pressure-at-peak dP/dt signal (20s or 120s) of the selected channel is applied via its input SVRb.

The third variable in the above relationship, namely, the factor "F", is a "resistance factor" which is dependent on the physical elasticity characteristics of the particular cardiovascular system examined. This factor is relatively constant for each individual, being in the order of 40,000–50,000, and varies about plus-or-minus 10% among different subjects. If desired, this value can be pre-determined for each individual and pre-set into circuit SVR via its input SVRc by a manual factor-setting circuit 30 and displayed in display 31. However, this would not always be necessary since, in many applications, it is not as important to know the actual system vascular resistance (which may be fed via output SVRd to read-out 32) as it is to know of any changes in the system vascular resistance as they occur. Accordingly, in many applications it would only be necessary to introduce the approximate resistance factor "F", which as indicated above, would be in the order of 40,000–50,000, and then merely monitor the read-out 32 to indicate any changes in the system vascular resistance. However, if desired to know the actual value of the systemic vascular resistance, the resistance factor "F" may be determined for each individual, by first determining the systemic vascular resistance using conventional techniques, and then determining from it the factor "F". Once determined, this factor remains substantially the same for that individual.

The apparatus 2 further includes a cardiac output computation circuit CO which determines the cardiac output according to the following relationship:

$$CO = \frac{MAP - CVP}{SVR} \times R$$

wherein MAP is the mean arterial pressure; CVP is the central venous pressure; SVR is the systemic vascular resistance; and R is Reynolds factor.

The SVR value is inputted via input COa from the systemic vascular resistance circuit SVR. The mean arterial pressure MAP is inputted via input COb, and is either the radial mean pressure from output 10c, or the femoral mean pressure from output 100c, depending on which arterial pressure channel 10 or 100 produces the lower dP/dt as determined by the minimum-level-detector circuit MLD. The central venous pressure CVP is measured separately and is manually introduced via input COc by means of a manual setting circuit 34, although it will be appreciated that it could be introduced automatically by directly measuring the central venous pressure. Reynolds Factor R is a constant. The above computation made by the cardiac output circuit CO is outputted via terminal COd to a read-out unit 36.

Figure 1:
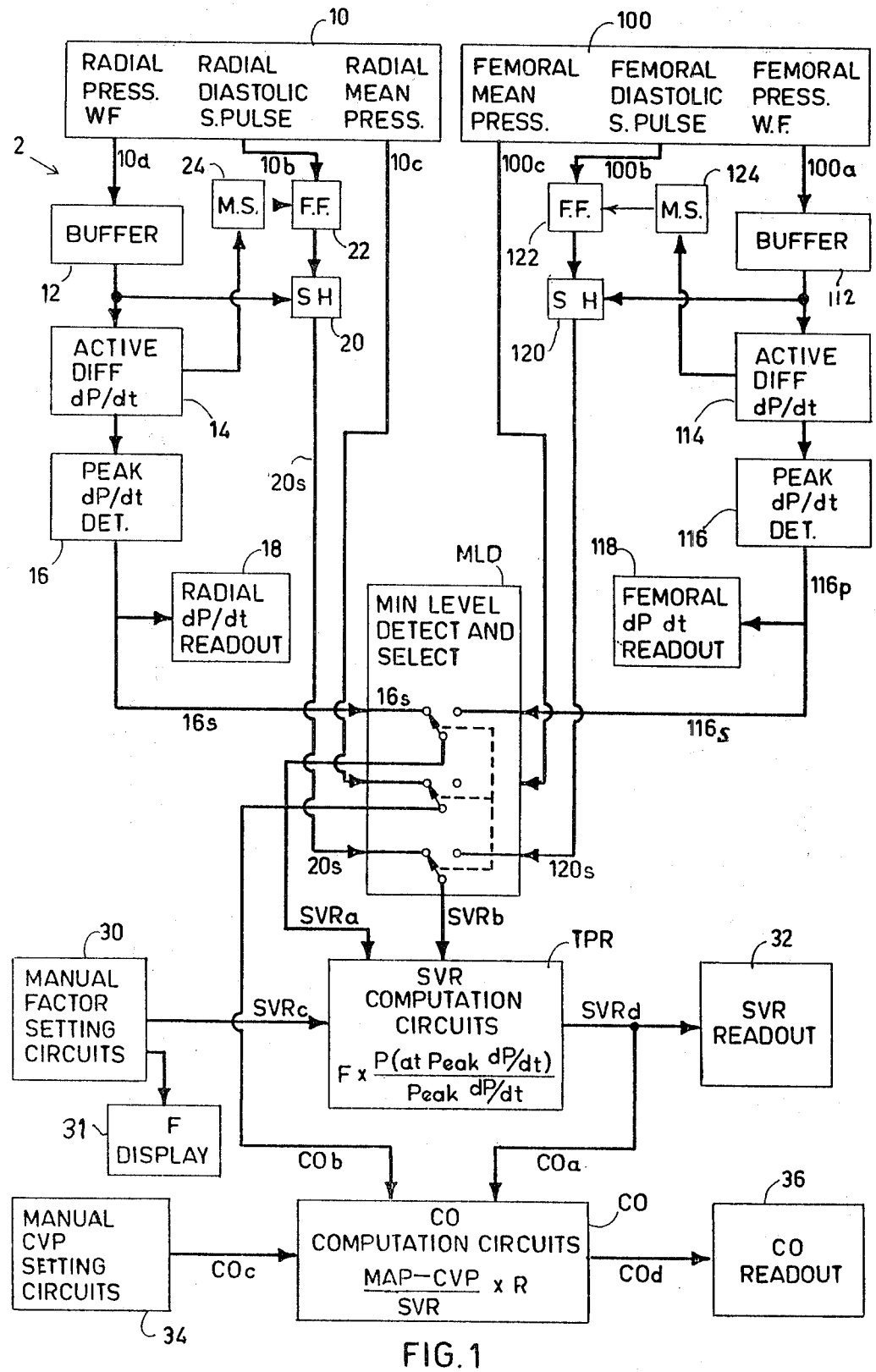
FIG. 1 is a functional block diagram of one form of apparatus constructed in accordance with the invention for examining and indicating the status of the cardiovascular system of a subject.

It will thus be seen that the apparatus illustrated in FIG. 1, by using only blood-pressure measurements obtainable from commercially-available equipment, computes and displays from these measurements both the systemic vascular resistance (i.e., the total peripheral resistance) and also the cardiac output, which measurements are particularly useful in assessing the status of a subject's cardiovascular system. These measurements produced by the illustrated system have been checked with those produced by the conventional invasive techniques, such as the above-described thermal dilution and dye dilution procedures, and have been found to produce results which bear a close relationship to those produced by these less-satisfactory invasive techniques.

While the system described above and illustrated in the drawings represents a preferred embodiment of the invention, it will be appreciated that many variations and modifications may be made. For example, the system could use only the one channel, e.g., the radial pressure channel, which would considerably simplify the system in that it would omit the other (femoral pressure) channel and also the minimum-level-detector circuitry MLD. In addition, when both channels are used, the lower value of dP/dt can be viewed by eye and selected by a manual selector rather than by using the minimum-level-detector circuit MLD. Also, as noted earlier, the pressure at peak dP/dt is almost equal to the diastolic pressure, and therefore the apparatus can be simplified by detecting and using the diastolic pressure, rather than by actually detecting the pressure at peak dP/dt. Further, the instruments for making the blood-pressure measurements (10a, 10b, 10c and 100a, 100b, 100c) could be embodied within the instrument 2, rather than be provided by separate commercially-available instruments. Still further, the peak dP/dt read-outs 18 and 118 are not essential and could be omitted.

Many other variations, modifications, and applications of the invention will be apparent.

What is claimed is:

1. A method of examining and indicating the status of the cardiovascular system of a subject, comprising the steps:
   A. detecting the arterial pressure of the subject and generating in response thereto a blood-pressure signal having a waveform in accordance with the detected arterial pressure;
   B. differentiating said blood-pressure signal to produce a dP/dt signal having a waveform varying in accordance with the rate at which the blood-pressure signal varies;
   C. detecting the peak of said dP/dt signal to determine the peak dP/dt;
   D. determining a value which is substantially equal to the arterial pressure at the time of said peak dP/dt;
   E. dividing said latter value by said peak dP/dt signal, thereby producing a measurement corresponding to the systemic vascular resistance of said cardiovascular system.

2. The method according to claim 1, wherein the value determined in step D is determined by detecting the arterial pressure at the time of said peak dP/dt.

3. The method according to claim 1, wherein the value determined in step D is determined by detecting the diastolic pressure.

4. The method according to claim 1, including the further step of:
- F. Multiplying the measurement produced in step E by a resistance factor corresponding to the physical resistance characteristics of the particular cardiovascular system examined, to produce a measurement of the systemic vascular resistance of the particular cardiovascular system examined.

5. The method according to claim 4, including the further steps of:
- G. producing a mean arterial pressure signal having a value corresponding to the mean arterial pressure of the subject;
- H. subtracting, from the latter signal, a signal corresponding to the subject's central venous pressure; and
- I. dividing the output of step H by the systemic vascular resistance signal of step F to produce a measurement corresponding to the cardiac output.

6. The method according to claim 5, wherein the systemic vascular resistance measurement of step F and the cardiac output measurement of step I are both continuously displayed.

7. The method according to claim 1 wherein the detected and processed arterial pressure is the radial pressure of the subject.

8. The method according to claim 1, wherein the detected and processed arterial pressure is either the radial pressure of the subject or the femoral pressure of the subject, having the lower dP/dt.

9. Apparatus for examining and indicating the status of the cardiovascular system of a subject, comprising:
- A. means for detecting the arterial pressure of the subject and generating in response thereto a blood-pressure signal having a waveform varying in accordance with the detected arterial pressure;
- B. means for differentiating said blood-pressure signal to produce a dP/dt signal having a waveform varying in accordance with the rate at which the blood-pressure signal varies;
- C. means for detecting the peak of said dP/dt signal to determine the peak dP/dt;
- D. means for determining a value which is substantially equal to the arterial pressure at the time of said peak dP/dt; and
- E. means for dividing said latter value by said peak dP/dt, thereby producing a measurement corresponding to the systemic vascular resistance of said cardiovascular system.

10. Apparatus according to claim 9, wherein said means D detects the arterial pressure at the time of said peak dP/dt, which pressure is used as the dividend by said means E.

11. Apparatus according to claim 9, wherein said means D detects the diastolic pressure, which pressure is used as the dividend by said means E.

12. Apparatus according to claim 9, further including:
- F. means for multiplying the measurement produced by said means E by a resistance factor corresponding to the physical resistance characteristics of the particular cardiovascular system examined, to produce a measurement of the systemic vascular Resistance of the particular cardiovascular system examined.

13. Apparatus according to claim 12, wherein said means F further includes manual pre-set means for introducing said resistance factor.

14. Apparatus according to claim 9, further including means for continuously displaying said systemic vascular resistance measurement.

15. Apparatus according to claim 9, further including:
- G. means for producing a mean arterial pressure signal having a value corresponding to the mean arterial pressure of the subject;
- H. means for subtracting, from the latter signal, a signal corresponding to the subject's central venous pressure; and
- I. means for dividing the output of means H by the systemic vascular resistance signal of means F to produce a measurement corresponding to the cardiac output.

16. Apparatus according to claim 15, wherein said apparatus further includes means for displaying said latter measurement.

17. Apparatus according to claim 9, wherein said means A detects and processes the radial pressure of the subject in a radial pressure channel.

18. Apparatus according to claim 17, wherein said means A also includes a separate femoral pressure channel which detects and processes the femoral pressure of the subject, said apparatus further including means for detecting the lower dP/dt in the two channels and for selecting in response thereto the corresponding pressure channel for processing.

19. Apparatus according to claim 9, wherein said means D comprises:
- (i) means for detecting the diastolic pressure of the subject and producing a diastolic sync pulse signal corresponding thereto;
- (ii) a bistable device actuated to a first state by said diastolic signal and to a second state by the peak dP/dt signal of means C; and
- (iii) a sample-and-hold circuit controlled by said bistable device, when in its second state, to sample said blood pressure signal of means B and to produce therefrom said pressure-at-peak-dP/dt signal.

* * * * *